United States Patent
Kim et al.

(10) Patent No.: US 12,138,412 B2
(45) Date of Patent: Nov. 12, 2024

(54) MICRO-ROBOT OPERATING DEVICE USING UNIDIRECTIONAL ULTRASONIC TRANSDUCER, AND SYSTEM USING SAME

(71) Applicant: KOREA INSTITUTE OF MEDICAL MICROROBOTICS, Gwangju (KR)

(72) Inventors: Chang-Sei Kim, Gwangju (KR); Jongoh Park, Gyeonggi-do (KR); Eunpyo Choi, Gwangju (KR); Byungjeon Kang, Gwangju (KR); Hansol Lee, Gwangju (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 854 days.

(21) Appl. No.: 17/293,556

(22) PCT Filed: Jan. 29, 2020

(86) PCT No.: PCT/KR2020/001378
§ 371 (c)(1),
(2) Date: May 13, 2021

(87) PCT Pub. No.: WO2020/171408
PCT Pub. Date: Aug. 27, 2020

(65) Prior Publication Data
US 2022/0001157 A1    Jan. 6, 2022

(30) Foreign Application Priority Data
Feb. 19, 2019  (KR) ........................ 10-2019-0019447

(51) Int. Cl.
*A61B 5/00*         (2006.01)
*A61B 34/00*       (2016.01)
(Continued)

(52) U.S. Cl.
CPC ............. *A61M 31/00* (2013.01); *A61B 34/72* (2016.02); *B25J 9/12* (2013.01)

(58) Field of Classification Search
CPC ............ A61M 31/00; A61B 34/72; B25J 9/12
See application file for complete search history.

(56) References Cited

U.S. PATENT DOCUMENTS

| 6,506,154 B1 | 1/2003 | Ezion et al. |
| 2019/0015070 A1* | 1/2019 | Memon ................. A61N 7/022 |

FOREIGN PATENT DOCUMENTS

| KR | 10-1083345 B1 | 11/2011 |
| KR | 10-1138323 B1 | 4/2012 |

(Continued)

OTHER PUBLICATIONS

International Search Report from corresponding PCT Application No. PCT/KR2020/001378, dated Aug. 13, 2020.

*Primary Examiner* — Joel F Brutus
(74) *Attorney, Agent, or Firm* — Harness, Dickey & Pierce, P.L.C.

(57) ABSTRACT

A micro-robot operating system using an ultrasonic transducer according to an embodiment of the present invention may comprise: a micro-robot moving in an inspection object; and a micro-robot operating device for controlling the location of the micro-robot. A micro-robot operating device using an ultrasonic transducer may comprise: an ultrasonic transducer unit including a plurality of ultrasonic transducers; and a control unit for controlling the plurality of ultrasonic transducers, wherein the plurality of ultrasonic transducers are arranged to form a curved surface toward a particular location in a space.

6 Claims, 8 Drawing Sheets

(51) Int. Cl.
*A61M 31/00* (2006.01)
*B25J 9/12* (2006.01)

(56) References Cited

FOREIGN PATENT DOCUMENTS

| KR | 10-1273302 | B1 | 6/2013 |
| KR | 10-1497303 | B1 | 3/2015 |

* cited by examiner

2-Axis Motorized Ultrasonic Manipulation System

Ultrasonic Transducer Array System

MICRO-ROBOT OPERATING DEVICE USING UNIDIRECTIONAL ULTRASONIC TRANSDUCER, AND SYSTEM USING SAME

CROSS-REFERENCE TO RELATED APPLICATIONS

This application is a national phase application of PCT Application No. PCT/KR2020/001378, filed on Jan. 29, 2020, which claims benefit of Korean Patent Application 10-2019-0019447, filed on Feb. 19, 2019. The entire disclosure of the applications identified in this paragraph are incorporated herein by references.

TECHNICAL FIELD

The present disclosure has been made according to project number HI19C0642 under the support of the Ministry of Health and Welfare, the research management institution for the above project is the Korea Health Industry Development Institute, the title of the research business is "Development of Technology and Commercialization for Medical Micro-robots", the title of the research project is "Common Basis Technology Development Center for Commercialization of Medical Micro-robots", the host organization thereof is the Korea Institute of Medical Micro-robotics, and the research period thereof is Jun. 12, 2019 to Dec. 31, 2022.

The present disclosure relates to a microrobot driving apparatus using unidirectional ultrasonic transducers and a system using the same, and more particularly, to an apparatus and system for wirelessly controlling the locations of microrobots within a target specimen by using a microrobot driving apparatus including unidirectional ultrasonic transducers arranged to be directed toward a specific location.

BACKGROUND ART

Among conventional driving apparatuses for moving a microrobot, an electromagnetic driving apparatus has problems with its large size and weight along with the problems with a low capture capability, a possibility of excessive administration of medication, and the use of magnetic particles.

Accordingly, an ultrasonic field driving apparatus for replacing the electromagnetic driving apparatus emerged. The ultrasonic field driving apparatus is basically divided into methods of controlling a microrobot by using a standing wave and using a difference between the phases of ultrasonic waves that unidirectionally travel.

First, the standing wave is formed by overlapping ultrasonic waves by using a plurality of ultrasonic transducers or by overlapping reflected ultrasonic waves by using an ultrasonic transducer and a reflector. When the standing wave is formed, an acoustic radiation force is generated toward an area having low pressure (an area having a low acoustic potential) within a corresponding area, that is, a pressure node. Microrobots spread near the area are captured at the pressure node. The microrobots captured within the acoustic field of the standing wave are moved in response to a change in the location of the pressure node. In this case, examples of a method used include two types of frequency control and phase control. If a frequency is changed, a standing wave is generated again based on the frequency, and the location of the node present at an interval of a wavelength half the wavelength of the frequency is also changed. The microrobots are captured again at the changed location of the node, and movements thereof can be controlled. In a method of assigning a difference between phases, the location of the node and a movement of captured particles can be controlled by simultaneously changing the phases of two ultrasonic transducers that face each other.

However, if the arrangement of ultrasonic transducers is used, the ultrasonic transducers cannot penetrate through an obstacle, such as a bone, and cannot be applied to the obstacle when the obstacle is present if the ultrasonic transducers are used in the human body. If a reflector is used, there is a problem in that the generation of a stable standing wave is limited because regular reflection and diffused reflection occur depending on states of a medium and a reflection wall. A conventional driving system can implement a movement of a microrobot by using a standing wave on a single medium. However, if the conventional driving system is applied to the human body including an irregular medium, there is a problem in the generation of a standing wave. The formation of a standing wave through the arrangement of ultrasonic transducers is limited due to a reflection phenomenon occurring in a bone when ultrasonic waves travel within the human body. Furthermore, a method of forming a standing wave by using reflection waves generated due to a change in a medium within the human body has a difficulty in forming a stable standing wave area due to regular reflection and diffused reflection occurring depending on states of a medium and a reflection wall.

A driving system using a unidirectional ultrasonic transducer array is a method of forming a focal zone for capture by using an arrangement and structural shapes of ultrasonic transducers and controlling microrobots through stage and phase control after the capture. In general, in the case of a unidirectional driving system, a focal zone is formed by focusing ultrasonic waves. In a conventional driving system using a unidirectional ultrasonic transducer array, a method of using structural shapes of ultrasonic transducers is used as a method of focusing ultrasonic waves. In this case, the focusing based on structural shapes is fixed because the location of a focus is mechanically designed and formed, and has problems in that it is difficult to move a microrobot captured in a focal zone in order to drive the microrobot. Furthermore, the microrobots can be captured and moved only at a place where the ultrasonic transducer is disposed, and the radius of control of the microrobot may be further limited depending on a structural characteristic of an arrangement.

A sound wave has a property that the sound wave travels through the vibration of a medium. For this reason, assuming that the sound wave passes through two different media, permeability or reflexibility is different depending on unique acoustic resistance (density X the speed of a sound) of each medium. If an acoustic resistance difference between the two different media is small, ultrasonic waves smoothly travel because reflexibility is small and permeability is high. However, if the acoustic resistance difference between the two different media is great, permeability may be low because most of sound waves are reflected. That is, if external ultrasonic waves are delivered to the human body through the air without an intermediate medium, a large amount of the external ultrasonic waves is reflected in the air due to a great acoustic resistance difference between the air and a human body tissue, which may not generate a sufficient force for the capture of microrobots, that is, a key point to the driving of ultrasonic waves.

Accordingly, there is a recent need for a method for solving such problems.

SUMMARY

Technical Problem

An object of the present disclosure is to propose a driving apparatus for precisely controlling microrobots within a space by using a unidirectional ultrasonic transducer array and a system using the same.

Specifically, the driving apparatus for precisely controlling microrobots within a space by using the unidirectional ultrasonic transducer array according to the present disclosure and the system using the same propose a method for solving a conventional problem in that microrobots can be captured or moved only in a place where ultrasonic transducers are disposed and smoothly performing the capture of microrobots for the driving of ultrasonic waves by reducing reflexibility even when an acoustic resistance difference between media is great.

Technical Solution

A microrobot driving system using ultrasonic transducers according to an embodiment of the present disclosure for solving the aforementioned problems may include a microrobot injected into a subject; and a microrobot driving apparatus configured to control the location of the microrobot.

A microrobot driving apparatus using ultrasonic transducers according to an embodiment of the present disclosure may include an ultrasonic transducer unit including a plurality of ultrasonic transducers and a control unit configured to control the plurality of ultrasonic transducers, wherein the plurality of ultrasonic transducers is arranged to form a curved surface in a way to be directed toward a specific location in a space, the control unit applies a signal to each ultrasonic transducer, included in the plurality of ultrasonic transducers, with a time delay in order to change a location of a focus, and the focus indicates a vertical height where microrobots are disposed with respect to the ultrasonic transducer unit.

The microrobot driving apparatus using ultrasonic transducers according to an embodiment of the present disclosure may further include a motor stage unit for adjusting a location on a plane identical with a plane of the ultrasonic transducer unit, wherein the control unit controls the motor stage unit.

A microrobot driving apparatus using ultrasonic transducers according to an embodiment of the present disclosure may further include an interface including a liquid medium, wherein the interface is disposed between the microrobot driving apparatus and a space where the microrobots are disposed.

The plurality of ultrasonic transducers of the microrobot driving apparatus using ultrasonic transducers according to an embodiment of the present disclosure is divided into n areas, each having a fan shape and having a central angle of 360°/n (n is an integer equal to or greater than 2), and is configured and driven so that a phase difference between neighboring areas is sequentially increased or decreased by $2\pi/n$.

Advantageous Effects

The driving apparatus for precisely controlling microbots by using the unidirectional ultrasonic transducer array and the system using the same according to the present disclosure can capture and move microrobots and thus improve the targeting of the microrobots and efficiency of medication transfer. Furthermore, the system can have a reduced size and weight compared to the electromagnetic driving apparatus, and has a relatively low amount of electricity used. Furthermore, the system has compatibility with a medical ultrasonic probe and facilitates precise control because both imaging and driving can be performed by using the ultrasonic diagnosis probe together.

BEST MODE

A microrobot driving apparatus using ultrasonic transducers includes an ultrasonic transducer unit comprising a plurality of ultrasonic transducers and a control unit controlling the plurality of ultrasonic transducers, wherein the plurality of ultrasonic transducers is arranged to form a curved surface in a way to be directed toward a specific location in a space, the control unit applies a signal to each ultrasonic transducer, included in the plurality of ultrasonic transducers, with a time delay in order to change a location of a focus, and the focus indicates a vertical height where microrobots are disposed with respect to the ultrasonic transducer unit.

DETAILED DESCRIPTION

Hereinafter, preferred embodiments according to the present disclosure are described in detail with reference to the accompanying drawings. A detailed description to be disclosed below along with the accompanying drawings is to describe an exemplary form of the present disclosure and is not intended to describe a unique embodiment of the present disclosure.

The present embodiments are provided to only complete the present disclosure and to allow a person having ordinary knowledge in the art to which the present disclosure pertains to fully understand the category of the present disclosure. The present disclosure is merely defined by the category of the claims.

In some cases, in order to avoid making the concept of the present disclosure vague, a known structure or device may be omitted or may be illustrated in the form of a block diagram based on a core function of each structure or device. Furthermore, in the entire specification, the same element is described using the same reference numeral.

In the entire specification, when it is said that any part "comprises or includes" any element, it means that the part does not exclude any element, but may further include another element unless explicitly described to the contrary.

Furthermore, a term " . . . unit" described in the specification means a unit for processing at least one function or operation, and the unit may be implemented by hardware or software or a combination of hardware and software. Furthermore, "a or an", "one", and similar related words thereof may be used as a meaning including both singular and plural forms unless they are differently indicated in this specification or are evidently contradicted by the context.

Furthermore, specific terms used in embodiments of the present disclosure are provided to help understanding of the present disclosure. All terms used herein, including technical or scientific terms, have the same meanings as those commonly understood by a person having ordinary knowledge in the art to which the present disclosure pertains, unless defined otherwise. The use of such specific terms may be changed into another form without departing from the technical spirit of the present disclosure.

Hereinafter, preferred embodiments according to the present disclosure are described in detail with reference to the accompanying drawings. A detailed description to be disclosed below along with the accompanying drawings is to describe an exemplary form of the present disclosure and is not intended to describe a unique embodiment for carrying out the present disclosure.

A driving system using a unidirectional ultrasonic transducer array is a method of forming a focal zone for capture by using an arrangement and structural shapes of ultrasonic transducers and controlling microrobots through stage and phase control after the capture.

In general, a unidirectional driving system forms a focal zone by focusing ultrasonic waves. A method of using structural shapes of ultrasonic transducers and a method of using the arrangement of multiple ultrasonic transducers are used as the method of focusing ultrasonic waves. In the case of the focusing based on structural shapes, an additional system needs to be additionally used in order to change the location of a focus because the location of the focus is mechanically designed and formed.

Accordingly, in the present disclosure, a microrobot driving apparatus capable of adjusting the location of a focus through control of the phases of ultrasonic transducers by focusing ultrasonic waves through an ultrasonic transducer array without an additional system and a microrobot driving system using the same are described.

The microrobot driving system using ultrasonic transducers may be configured to include microrobots moving within a target specimen and a microrobot driving apparatus configured to control the locations of the microrobots.

A microrobot according to an embodiment of the present disclosure means all objects whose movement is controlled by the driving apparatus using ultrasonic transducers, and should be interpreted as having a broad sense meaning which may include even a solid particle consisting of a single component and bubble particles within a fluid.

A microrobot according to an embodiment of the present disclosure does not need to be fabricated using a specific method or to include a specific component. This is an advantage of the driving of ultrasonic waves in the present disclosure. If the driving system of the present disclosure is used, microbots can be captured regardless of the type or component of a control subject. Specifically, for example, if a standing wave is formed by ultrasonic waves within a small chamber, various particles, such as protein, nucleic acid, red blood cells, biocompatible polymer, and chemical substances, may be captured without restriction. Furthermore, according to an acoustic radiation force equation, even air bubbles within a fluid having high compressibility can be captured at an anti-node in which high pressure is formed, not a pressure node. Accordingly, the driving system is characterized in that even various bubbles within a fluid can be captured without restriction. From the nature of the acoustic radiation force, if any particle composed of any material has higher density than a medium within an acoustic field, the particle can be captured using the transducer system and phase control method according to the present disclosure. In the present disclosure, it is preferred that the microrobot, that is, a particle to be captured, is a particle having a diameter smaller than the wavelength of a frequency used to drive ultrasonic waves. In general, if the diameter of a particle is smaller than a half wavelength, the particle can be stably captured. As a detailed example, a nanoparticle and a microparticle, each one having a diameter much smaller than the wavelength of ultrasonic waves used in the transducer and having higher density than a fluid medium of an acoustic field, can be stably captured.

In particular, a particle described in this specification may include a microrobot. Hereinafter, a microrobot whose movement is controlled by the driving apparatus using ultrasonic transducers according to the present disclosure may receive a driving force by ultrasonic waves.

Hereinafter, a particle driving apparatus using ultrasonic transducers and a system using the same are described in detail.

Figure 1:
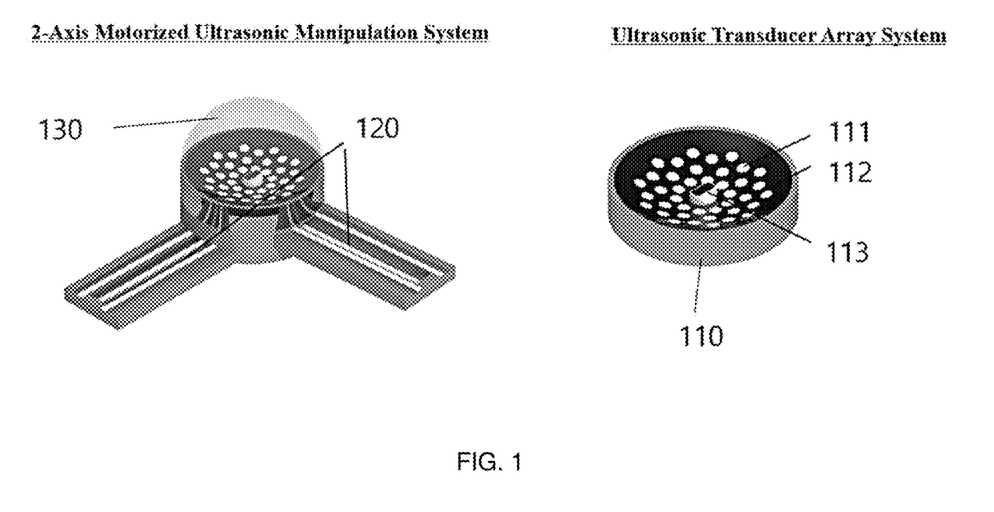
FIG. 1 is an embodiment of the present disclosure, and is a diagram illustrating a driving apparatus for controlling movements of microrobots by using a unidirectional ultrasonic transducer array.

FIG. 1 is an embodiment of the present disclosure, and is a diagram illustrating a driving apparatus for controlling movements of microrobots by using a unidirectional ultrasonic transducer array.

A drawing on the left side of FIG. 1 illustrates an example of the driving apparatus for controlling movements of microrobots by using a unidirectional ultrasonic transducer array according to the present disclosure. The driving apparatus for controlling movements of microrobots by using the unidirectional ultrasonic transducer array may be configured to include at least one of an ultrasonic transducer unit 110, a motor stage unit 120, an interface unit 130 and a control unit which are arranged.

A drawing on the right side of FIG. 1 illustrates the ultrasonic transducer unit 110. A plurality of ultrasonic transducers 111 may be disposed on a curved surface of the ultrasonic transducer unit 110, and may be arranged to indicate a specific location on the ultrasonic transducer unit and to form an ultrasonic transducer array 112. Furthermore, an ultrasonic probe 113 for implementing an image may be disposed at the center of the ultrasonic transducer unit.

The drawing on the left side of FIG. 1 illustrates an integrated ultrasonic transducer driving apparatus including the planar motor system 120 and the interface 130 along with the ultrasonic transducer unit 110. The ultrasonic transducer unit 110 may be disposed at the center of the ultrasonic transducer driving apparatus. An XY planar motor system, that is, the motor stage unit 120, may be disposed in the peripheries of the ultrasonic transducer unit 110. Furthermore, the interface 130 may be applied or disposed to come into contact with the ultrasonic transducer unit or with a given distance between the interface 130 and the ultrasonic transducer unit.

The interface 130 is for minimizing reflection according to a change in ultrasonic waves of a medium, and is used for the role of a contact medium between the ultrasonic transducer driving apparatus or the system and the human body. The interface 130 uses a material, such as silicon similar to a tissue of the human body. The inside of the interface is filled with a liquid medium, such as gel applied upon checking of the ultrasonic waves, thereby removing an air layer between the ultrasonic transducers and the interface. Gel is applied to a surface of silicon to bring the gel into contact with the human body, thereby minimizing a reflection effect attributable to a change in the medium upon checking of the ultrasonic waves.

The control unit may transmit, to each module or unit, an instruction or signal for controlling at least one of the ultrasonic transducer unit 110, the motor stage unit 120, and the interface 130 included in the driving apparatus for controlling movements of microrobots by using the unidirectional ultrasonic transducer array, or may receive and process a signal or information collected from each module or unit.

As an example in which the control unit controls the modules or units within the driving apparatus for controlling movements of microrobots by using the unidirectional ultrasonic transducer array, Z-axis driving of microrobots is controlled through control of the phase of each of the ultrasonic transducers 111 within the ultrasonic transducer unit 110, and the microrobots are driven on an XY plane (a plane parallel to the outmost surface of the ultrasonic transducer) through the motor stage unit 120, thus implementing three-dimensional driving in an integrated way.

Figure 2:
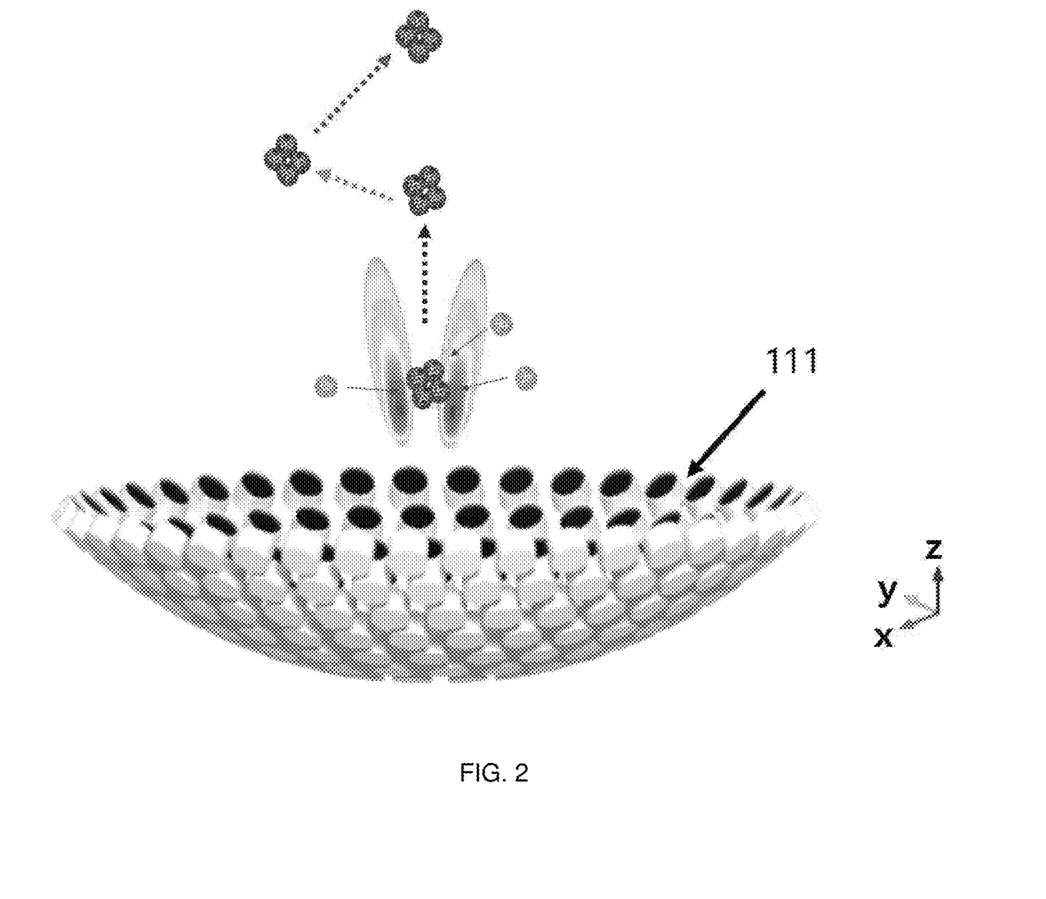
FIG. 2 is an embodiment of the present disclosure, and is a diagram illustrating an example of an array of a plurality of ultrasonic transducers.

FIG. 2 is an embodiment of the present disclosure, and is a diagram illustrating an example of an array of the plurality of ultrasonic transducers.

As illustrated in FIG. 2, the ultrasonic transducers 111 may be arranged and configured as a curved structure. The plurality of ultrasonic transducers 111 may be arranged to indicate a specific location. The specific location indicated by the plurality of ultrasonic transducers 111 may be a location on a space over the ultrasonic transducers.

Ultrasonic waves are focused to form a focal zone by a structural characteristic. A characteristic of an acoustic field is determined through a method of controlling the phases of the ultrasonic transducers 111. If a signal is applied by assigning time delay (a time delay) to the ultrasonic transducers 111, a difference may be assigned to the phases of the ultrasonic transducers. Accordingly, the location of a structurally set focus can be changed. In the present disclosure, the location of a focus is intensively used to change a direction perpendicular to the ultrasonic transducer array. An embodiment in which the location of a focus is changed through phase control is described later with reference to FIGS. 5a and 6.

Figure 3:
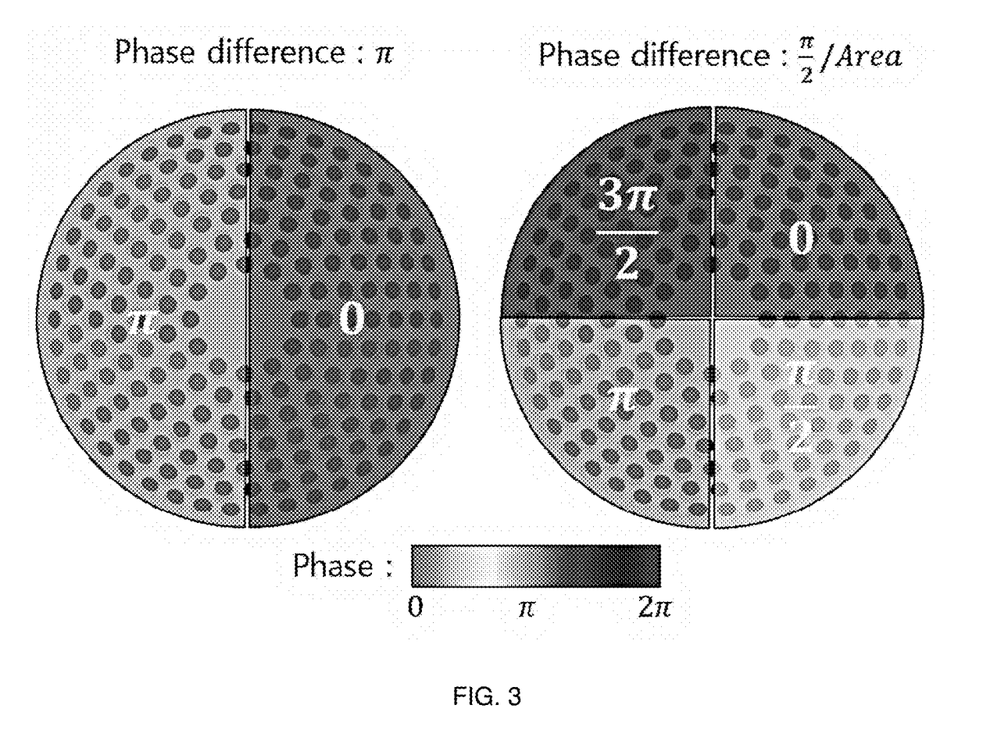
FIG. 3 is an embodiment of the present disclosure, and is a diagram illustrating an example of areas in which phase differences are assigned to the ultrasonic transducers arranged within an ultrasonic transducer unit.

FIG. 3 is an embodiment of the present disclosure, and is a diagram illustrating an example of areas in which phase differences are assigned to the ultrasonic transducers arranged within the ultrasonic transducer unit.

As illustrated in FIG. 3, when the ultrasonic transducer array is viewed from the top, an ultrasonic acoustic field in which microrobots can be captured may be formed by assigning a phase difference to each area.

Specifically, the plurality of ultrasonic transducers is divided into n areas each having a fan shape and having a central angle of 360°/n (n is an integer equal to or greater than 2). A phase difference between neighboring areas is set to be sequentially increased or decreased by $2\pi/n$, so that the ultrasonic transducers may form an ultrasonic acoustic field.

As a detailed example, a drawing on the left side of FIG. 3 illustrates a case where the plurality of ultrasonic transducers is divided into two areas and a phase difference of $\pi$ (180°) is assigned to each of the two areas. If the phase difference of $\pi$ (180°) is assigned to each of the two areas, a strong acoustic radiation force for a push from the left and right areas where high pressure is formed to the center is generated.

As a detailed example, a drawing on the right side of FIG. 3 illustrates a case where the plurality of ultrasonic transducers is divided into four areas and a phase difference is assigned to each of the four areas by $\pi/2$ (90°). If the phase difference is assigned to each of the four areas at intervals of $\pi/2$, an acoustic field is formed like a whirlwind. An acoustic radiation force is generated in the direction toward the center from a surrounding area where pressure is strong.

Figure 4:
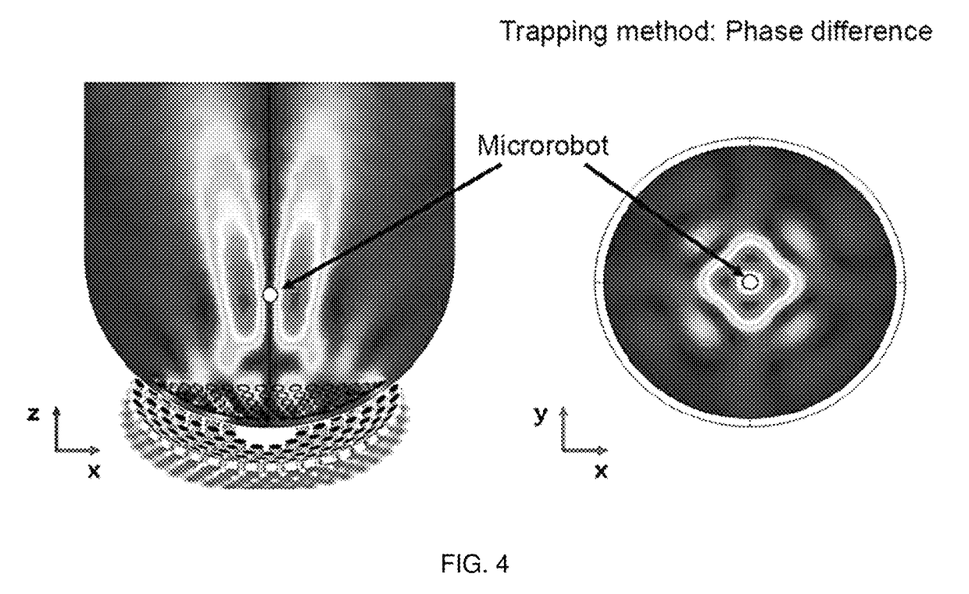
FIG. 4 is an embodiment of the present disclosure, and is a diagram illustrating an example in which an acoustic field was analyzed when phase differences each being $\pi/2$ (90°) were assigned to the plurality of ultrasonic transducers divided into four areas.

FIG. 4 is an embodiment of the present disclosure, and is a diagram illustrating an example in which an acoustic field was analyzed when the plurality of ultrasonic transducers was divided into four areas and a phase difference of $\pi/2$ (90°) was assigned to each of the four areas.

If the plurality of ultrasonic transducers is divided into the four areas and the phase difference of $\pi/2$ (90°) is assigned to each of the four areas, an acoustic field is formed in a whirlwind direction because a surrounding area distant from a focus has higher pressure than a focal zone close to the focus. As a result, an acoustic radiation force is generated toward the focal zone. Accordingly, as illustrated in FIG. 4, microrobots will be captured in the focal zone having low pressure within the acoustic field. In FIG. 4, when viewed from the top, the microrobots will be captured at a place where pressure is low and which is present at the center indicated in red.

As described above, an ultrasonic acoustic field is formed by dividing the plurality of ultrasonic transducers into n areas, each having a fan shape and having a central angle of 360°/n (n is an integer equal to or greater than 2), and setting a phase difference between neighboring areas to be sequentially increased or decreased by $2\pi/n$. In addition, a movement in the Z-axis direction of a focus, that is, a location where particles are captured, can be controlled by applying time delay depending on the distance of each transducer from the center of the transducer unit.

Figure 5A:
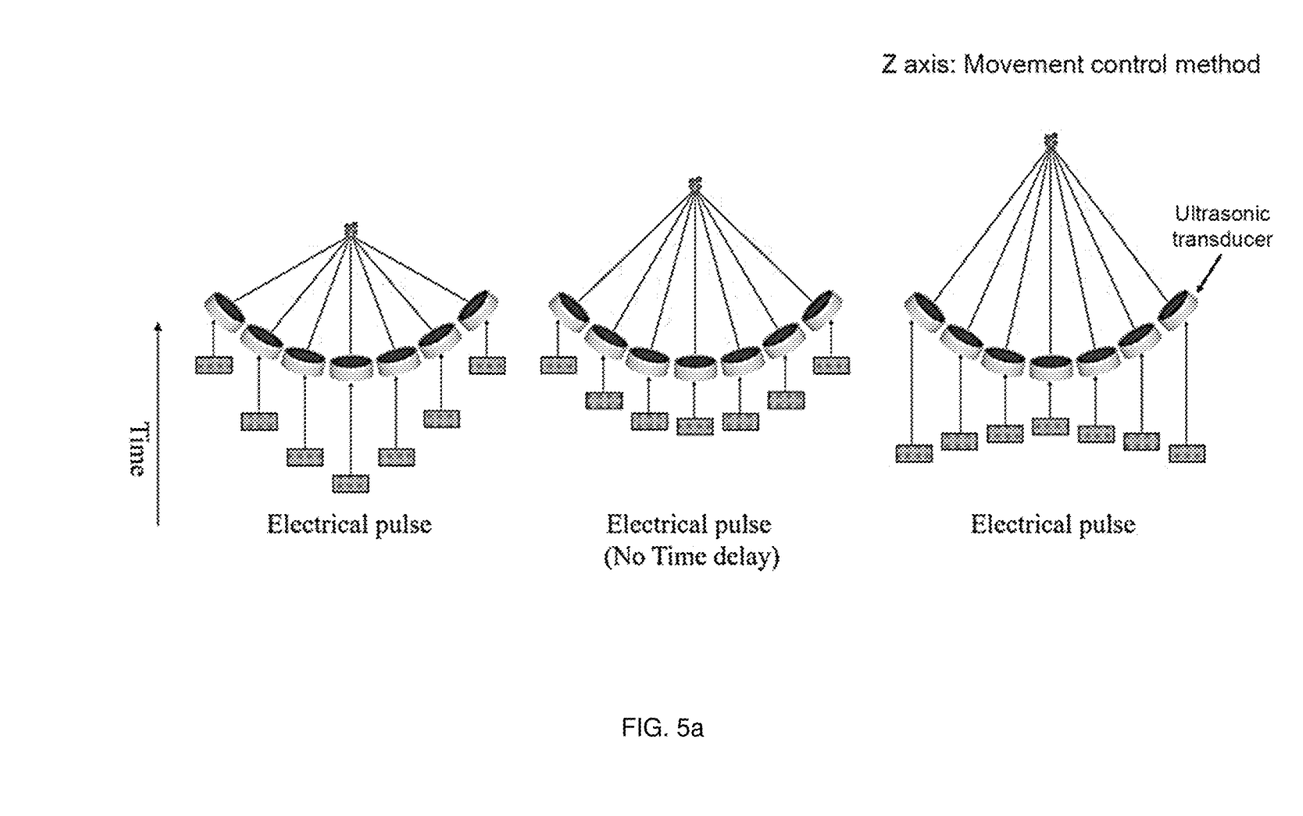
FIG. 5a is an embodiment of the present disclosure, and is a diagram illustrating an example of a method of controlling movements of captured microrobots through time delay.

FIG. 5a is an embodiment of the present disclosure, and is a diagram illustrating an example of a method of controlling movements of captured microrobots through time delay.

As illustrated in FIG. 5a, the control unit may control a distance between captured particles and each ultrasonic transducer based on time delay of a signal applied to the ultrasonic transducer 111. A focus or a focal zone may indicate a place where microrobots are crowded. A distance between the focus or the focal zone and the ultrasonic transducer may be controlled through a phase difference. Furthermore, phase control may be performed based on time delay of a signal applied to each ultrasonic transducer.

The time delay is for generating a phase difference between application signals applied to the transducers. The location of a focus is not changed by differently setting only the time delay. When a sine wave is applied as an application signal and one cycle of the signal has a phase of $2\pi$, if the phase of the application signal is changed within 2π through time delay, a change in the location of a focus may be controlled as in FIG. 5a.

Figure 5B:
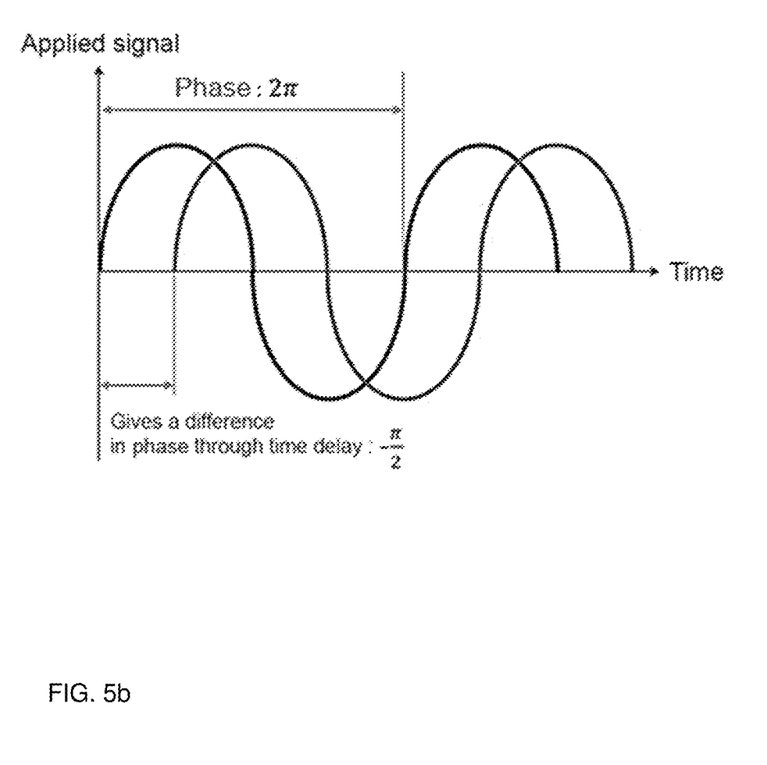
FIG. 5b illustrates an example in which the ultrasonic transducers are disposed on a plane, and illustrates a concept that phase differences are assigned based on time delay.

FIG. 5b is a diagram illustrating an example in which the transducers are disposed on a plane. When the transducers are disposed in a curved manner as in FIG. 5a, if phase differences are assigned as illustrated in FIG. 5b, an improved collection effect occurs in the state in which a focus has been formed. Accordingly, the focus is formed on the lower side. Furthermore, if time delay is applied toward the outside as in FIG. 5a, the focus is upward moved.

For example, as illustrated in FIG. 5a, as a difference (time delay) between the time when a signal is applied to an ultrasonic transducer disposed at the center of the array of the plurality of ultrasonic transducers 111 and the time when a signal is applied to an ultrasonic transducer disposed in the peripheries of the array is small, that is, the time delay becomes short, a distance between the ultrasonic transducer and a focal zone becomes close. On the contrary, as a difference (time delay) between the time when a signal is applied to the ultrasonic transducer disposed in the peripheries of the array of the plurality of ultrasonic transducers and the time when a signal is applied to the ultrasonic transducer disposed at the center of the array is large, that is the time delay becomes long, a distance between the focal zone and the ultrasonic transducer becomes gradually distant.

Figure 6:
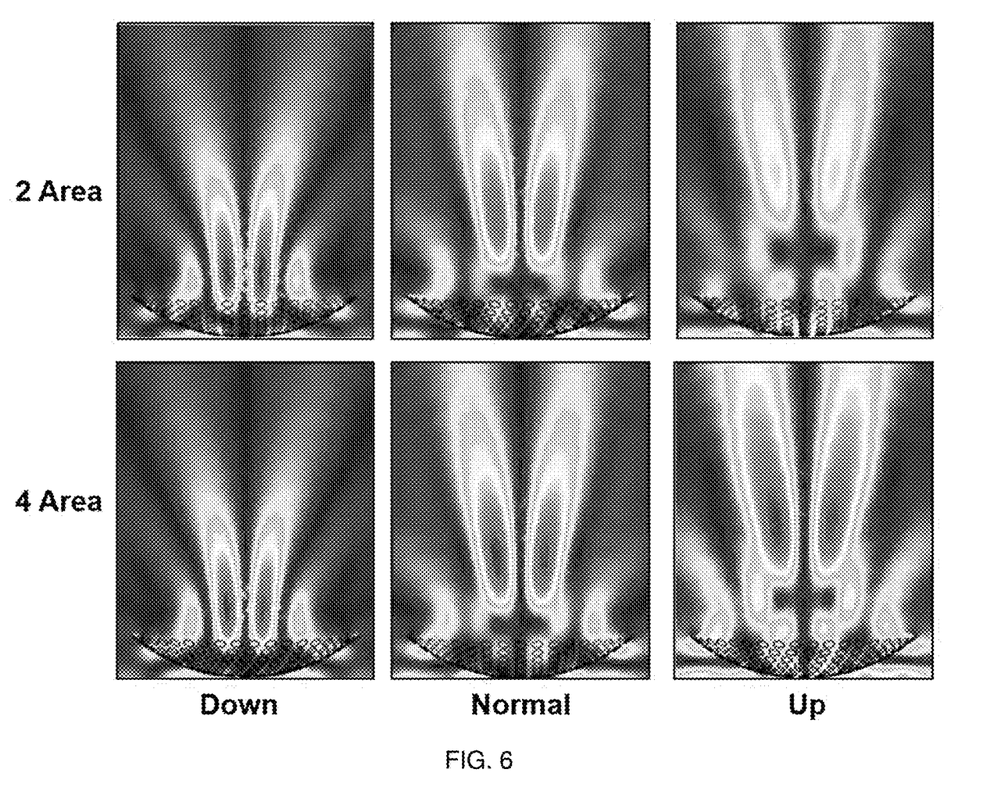
FIG. 6 is an embodiment of the present disclosure, and is a diagram illustrating the results of simulations for controlling a distance between microrobots and ultrasonic transducers by assigning phase differences based on time delay.

FIG. 6 is an embodiment of the present disclosure, and is a diagram illustrating the results of simulations for controlling a distance between microrobots and ultrasonic transducers by assigning phase differences based on time delay.

In the simulations, an array system of ultrasonic transducers was assumed to have a diameter of about 15 cm. In FIG. 6, three continuous images are the results of the simulations showing a change in a focus checked through additional phase control after assigning phase differences to two areas (each having a phase difference of π) and four areas (each having a phase difference of π/2).

The verification of up and down control of a focal zone through phase control of the focal zone within an acoustic field may be checked through the results of simulations. Three images on the upper side of FIG. 6 correspond to a case where the phase differences were assigned to the two areas at intervals of π. Three images on the lower side of FIG. 6 correspond to a case where the phase differences were assigned to the four areas at intervals of π/2. From FIG. 6, it can be seen that the location of the focal zone where microrobots are captured can be controlled through phase control.

If a phase difference for a focus is not assigned, a focus is formed as in a middle drawing (Normal) of FIG. 6. As described above, if ultrasonic transducers are disposed as a flexural structure whose middle portion is hollow, a focus is formed at the center due to a structural influence although phase differences are not assigned to the ultrasonic transducers. Of course, in order to capture microrobots, phase differences need to be assigned to form an area having low pressure.

As illustrated in the drawing (Down) on the left side of FIG. 6, if great time delay is applied to a signal or a phase is subtracted from an ultrasonic transducer at the center of the array to an ultrasonic transducer at an edge of the array, a focus is formed on the lower side compared to the focus in the middle drawing (Normal).

On the contrary, as illustrated in the drawing (Up) on the right side of FIG. 6, if small time delay is applied to a signal or a phase is added from an ultrasonic transducer at the center of the array to an ultrasonic transducer at an edge of the array, a focus is formed on the upper side compared to the focus in the middle drawing (Normal).

A method of controlling movements of microrobots up and down (Z axis) with respect to the ultrasonic transducers has been described with reference to FIGS. 5a and 6. Hereinafter, the microrobot driving apparatus including the interface for minimizing reflection attributable to a movement within a plane (XY plane) parallel to the plurality of ultrasonic transducers, along with a Z-axis movement, and a change in an ultrasonic medium is described.

Hereinafter, effects of the present disclosure are described by describing the contents of experiments through the driving apparatus for controlling movements of microrobots by using the unidirectional ultrasonic transducer array with reference to FIG. 7.

Figure 7:
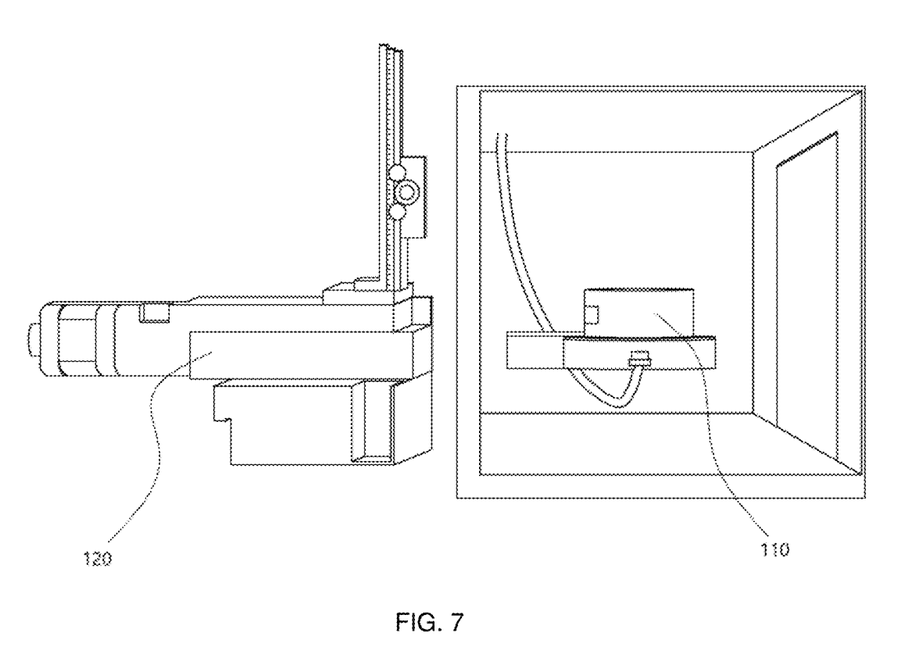
FIG. 7 is an experiment setting photograph for verifying basic experiments for the driving of ultrasonic waves.

FIG. 7 is a photograph illustrating an embodiment of the ultrasonic driving system.

FIG. 7 shows an example in which the ultrasonic transducer unit 110 and the motor stage unit 120 are implemented.

As described through the aforementioned results, the driving apparatus for controlling movements of microrobots by using the unidirectional ultrasonic transducer array according to the present disclosure can drive microrobots by forming a focal zone on a three-dimensional space in a way to generate an acoustic field by assigning a phase difference to each area of ultrasonic transducers, thereby performing medical treatment on a portion (eyeball, etc.) with which a liquid medium is filled.

Furthermore, the ultrasonic driving system according to the present disclosure can capture and move multiple microrobots unlike the existing method using directionality and propulsion. This is effective in targeting toward an affected area when microrobots are driven and thus improves efficiency of medication transfer.

Furthermore, from the nature of each ultrasonic transducer, the size and weight of the system can be reduced, and the amount of electricity used is maintained at a low level. This has an advantage in that the system is cheap compared to the existing microrobot driving system.

A micro, a nanorobot and particles applied through the present disclosure can be controlled in a two-dimensional manner on a plane within a medium through the ultrasonic transducer array system and a two-axis motor system for forming an unidirectional focal zone, and can be induced to move in a three-dimensional manner through control of the location of a focus according to control of the phase of ultrasonic waves.

Furthermore, an ultrasonic probe for diagnosis now being used in a hospital can be used together to secure images and video of microrobots. Accordingly, it is possible to control movements of captured or surrounding particles disposed based on the images and video while checking the particles.

A person having ordinary knowledge in the technical field related to the embodiments of the present disclosure will understand that the present disclosure may be implemented in modified forms without departing from the essential characteristic of the description. Accordingly, the disclosed methods should be considered from a descriptive viewpoint, not a limitative viewpoint.

The scope of the present disclosure appears in the claims, not the detailed description of the present disclosure, and all differences within an equivalent range thereof should be construed as being included in the scope of the present disclosure.

DESCRIPTION OF REFERENCE NUMERALS

110: ultrasonic transducer unit
111: ultrasonic transducer
112: ultrasonic transducer array
113: ultrasonic probe
120: motor stage unit
130: interface unit

INDUSTRIAL APPLICABILITY

The present disclosure relates to a microrobot driving apparatus using unidirectional ultrasonic transducers and a system using the same, and more particularly, to an apparatus and system for wirelessly controlling the locations of microrobots within a target specimen by using a microrobot driving apparatus including unidirectional ultrasonic transducers arranged to be directed toward a specific location.

What is claimed is:

1. A microrobot driving apparatus using ultrasonic transducers, comprising:
    an ultrasonic transducer unit comprising a plurality of ultrasonic transducers; and
    a control unit controlling the plurality of ultrasonic transducers,
    wherein the plurality of ultrasonic transducers is arranged to form a curved surface in a way to be directed toward a specific location in a space,
    the control unit applies a signal to each ultrasonic transducer, included in the plurality of ultrasonic transducers, with a time delay in order to change a location of a focus, and
    the focus indicates a vertical height where microrobots are disposed with respect to the ultrasonic transducer unit,
    wherein the plurality of ultrasonic transducers is divided into n areas, each having a fan shape and having a central angle of 360°/n where n is an integer equal to or greater than 2, and is configured and driven so that a phase difference between neighboring areas is sequentially increased or decreased by $2\pi/n$.

2. The microrobot driving apparatus of claim 1, further comprising:
    a motor stage unit for adjusting a location on a plane identical with a plane of the ultrasonic transducer unit,
    wherein the control unit controls the motor stage unit.

3. The microrobot driving apparatus of claim 2, further comprising:
    an interface comprising a liquid medium,
    wherein the interface is disposed between the microrobot driving apparatus and a space where the microrobots are disposed.

4. A microrobot driving system using ultrasonic transducers, comprising:
    microrobots injected into a subject; and
    a microrobot driving apparatus controlling locations of the microrobots,
    wherein the microrobot driving apparatus comprises an ultrasonic transducer unit comprising a plurality of ultrasonic transducers and a control unit controlling the plurality of ultrasonic transducers,
    the plurality of ultrasonic transducers is arranged to form a curved surface in a way to be directed toward a specific location in a space,
    the control unit applies a signal to each ultrasonic transducer, included in the plurality of ultrasonic transducers, with a time delay in order to change a location of a focus, and
    the focus indicates a vertical height where microrobots are disposed with respect to the ultrasonic transducer unit,
    wherein the plurality of ultrasonic transducers is divided into n areas, each having a fan shape and having a central angle of 360°/n where n is an integer equal to or greater than 2, and is configured and driven so that a phase difference between neighboring areas is sequentially increased or decreased by $2\pi/n$.

5. The microrobot driving system of claim 4, wherein:
    the microrobot driving apparatus further comprises a motor stage unit adjusting a location on a plane identical with a plane of the ultrasonic transducer unit, and
    the control unit controls the motor stage unit.

6. The microrobot driving system of claim 4, wherein:
    the microrobot driving apparatus further comprises an interface comprising a liquid medium, and
    the interface is disposed between the microrobot driving apparatus and a space where the microrobots are disposed.

* * * * *